United States Patent [19]

Sato et al.

[11] Patent Number: 4,474,957

[45] Date of Patent: Oct. 2, 1984

[54] PROCESS FOR PRODUCING CYANURIC ACID FROM UREA

[75] Inventors: Soichi Sato; Shuzo Maeda; Junji Nakagi, all of Tokushima, Japan

[73] Assignee: Shikoku Chemicals Corporation, Japan

[21] Appl. No.: 441,272

[22] Filed: Nov. 12, 1982

[51] Int. Cl.³ ........................................ C07D 251/32
[52] U.S. Cl. ........................................ 544/192
[58] Field of Search ........................................ 544/192

[56] References Cited

U.S. PATENT DOCUMENTS 2,943,088 6/1980 Westfall .............................. 544/192
3,953,443 4/1976 Ohata et al. .............................. 544/192

*Primary Examiner*—John M. Ford
*Attorney, Agent, or Firm*—Steele, Gould & Fried

[57] ABSTRACT

There is disclosed a process for producing cyanuric acid from urea using an external heating type reaction vessel furnished with agitator provided with plural urea supply ports in the direction of conveyance of the contents at such an interval as to make the residence time of the contents about 2 to 20 minutes, heating the urea in the presence of crude cyanuric acid to a temperature of 230°-320° C. to subject it to heat decomposition, and recycling a part of the formed crude cyanuric acid to the reactor. According to this process, the urea corresponding to the amount not exceeding ⅓ in ratio by weight to the crude cyanuric acid to be used in circulation is fed respectively into the reaction vessel through each urea supply port, and, while preventing progress of adhesion of contents to the inner wall of the reaction vessel as well as the agitator and formation of blocks, the combined amount of the urea to be fed into the reaction vessel from each urea supply port is made to exceed substantially ⅓ in ratio by weight to the crude cyanuric acid to be used in circulation.

10 Claims, 1 Drawing Figure

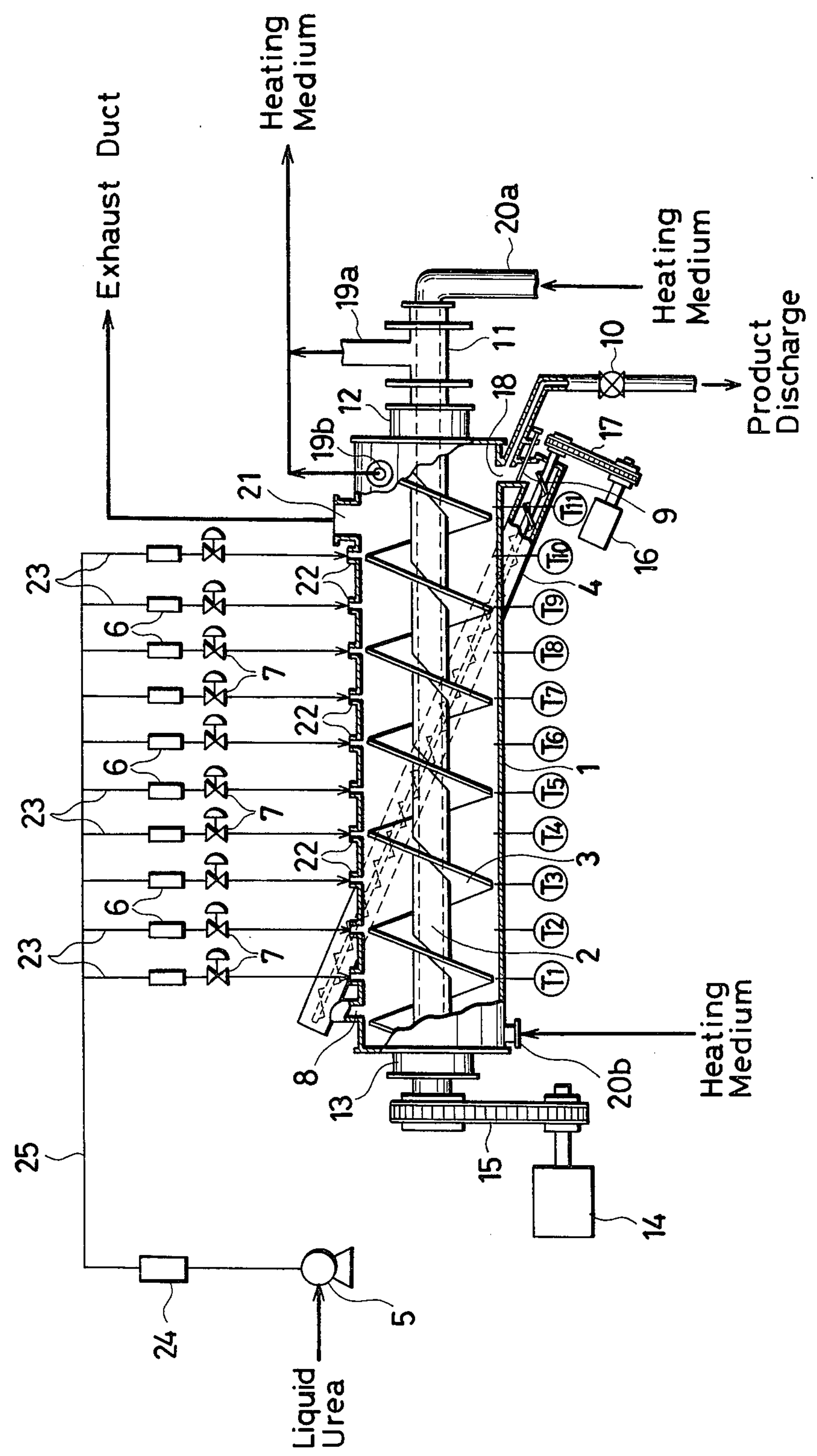
Exhaust Duct
Heating Medium
Heating Medium
Product Discharge
Heating Medium
Liquid Urea

PROCESS FOR PRODUCING CYANURIC ACID FROM UREA

BACKGROUND OF THE INVENTION

The present invention relates to a process for producing cyanuric acid by decomposing urea. More particularly, the invention provides extremely advantageous and economical process in an industrial process for producing cyanuric acid by subjecting urea to heat treatment by the use of an external heating type reaction vessel furnished with agitator such as a kneader or a paddle mill.

With regard to the process for producing cyanuric acid from urea, various procedures have already been known.

Hitherto it has been well known that, when urea is heated, decomposition reaction progresses through the change of states in order of solid state→transparent low viscosity liquid state→white turbid state→paste state→solid state until completion of reaction. Under the ordinary heat treatment process the reaction products adhere to the heat transfer surface and the agitator blades and take block form, thereby providing difficulty to continuous operation, and moreover, leading to lowering of yield. For these reasons, various methods to solve these problems have been proposed.

For example, U.S. Pat. No. 2,943,088 discloses a method for continuous production of crude cyanuric acid by feeding a part of crude cyanuric acid discharged from a kiln to a pug mill, adding a required amount of urea, and mixing, followed by recycling it to the kiln to produce crude cyanuric acid continuously.

Besides the above, Japanese patent publication No. 256,76/74 discloses a continuous process for producing crude cyanuric acid by pulverizing the crude cyanuric acid calcined at low temperature discharged from No. 1 pug mill, adding thereto a designed amount of urea, and mixing to form a low-temperature calcined crude cyanuric acid, pulverizing it and recycling a part of it to No. 1 pug mill, with the remainder fed to No. 2 pug mill to produce crude cyanuric acid continuously.

In these methods, in either case, supply ratio of urea to crude cyanuric acid is placed under restriction. Unless the crude cyanuric acid of about three fold amount or more to the urea in ratio by weight is recycled, smooth continuous operation cannot be maintained.

In other words, according to the present inventors' experience, when the amount of supply of the urea to the recycled amount of crude cyanuric acid exceeds about ⅓ in ratio by weight, adhesion of contents to the inner wall of the reactor and the agitator progress and generation of block products is caused, thus making it difficult to carry out continuous operation.

Accordingly, in order to secure smooth operation through these means, it is necessary to cycle three or more parts by weight of crude cyanuric acid to 1 or less part by weight of material urea to be supplied. This makes it necessary to enlarge remarkably the size of the reaction vessel. It accompanies degradation in production efficiency and loss of energy, etc. which cannot be accepted as a satisfactory condition.

SUMMARY OF THE INVENTION

An object of the present invention is to provide a process which makes it possible to produce continuously cyanuric acid in good efficiency without causing troubles for the reaction products to adhere to the inner wall of the reaction vessel as well as the agitator.

Another object of the present invention is to provide a process which makes it possible to increase the amount of supply of urea to the recycled amount of crude cyanuric acid and improve the yield of cyanuric acid.

A further object of the present invention is to provide a process by which the reaction vessel can be made as compact as possible.

According to the present invention, there is so designed that, in order to attain these objects, by the use of an external heating type reaction vessel provided with agitator having plural ports for supply of urea, the urea corresponding to the amount not exceeding ⅓ in ratio by weight to the crude cyanuric acid to be used in circulation is fed respectively into the reaction vessel through each urea supply port, and, while preventing progress of adhesion of contents to the inner wall of the reaction vessel as well as the agitator and formation of blocks, the combined amount of the urea to be fed into the reaction vessel is made to exceed substantially ⅓ in ratio by weight to the crude cyanuric acid to be used in circulation.

BRIEF DESCRIPTION OF THE DRAWING

The drawing is a schematic side view showing the reaction vessel to be used for the process of the present invention.

DETAILED DESCRIPTION

The present invention process is conducted by the use of an external heating type reaction vessel furnished with agitator provided with plural supply ports for urea at such intervals as to make the residence time of the contents 2 to 20 minutes in the direction of conveyance of the contents.

According to the process of the present invention, in a reaction vessel urea is heat decomposed in the presence of cyanuric acid at a temperature of 230° to 320° C. to have cyanuric acid formed. A part of the formed cyanuric acid is recovered from the reaction vessel, and the other part is recycled into the reaction vessel.

And, from each port for supply of urea the urea corresponding to no more than ⅓ in ratio by weight to the crude cyanuric acid which is used in circulation is supplied. The combined amount of the urea to be supplied from each supply port for material urea to the reaction vessel is made to exceed substantially ⅓ in ration by weight to crude cyanuric acid to be used in circulation.

As will be understood from the foregoing description, when the urea to be supplied through each port for supply of urea is less than ⅓ in ratio by weight to the crude cyanuric acid to be used in circulation, progress of adhesion of contents to the inner wall of the reaction vessel as well as the agitator and formation of block matter are prevented to make it possible to carry on continuous operation. Also, according to the experiments conducted by the present inventors, it is recognized that when urea is heated at 230° C., urea becomes solidified in 6 to 7 minutes to lose adhesiveness, and similarly, when it is heated at a temperature of about 240° C., it becomes solidified in 5–6 minutes, at about 250° C. in 4–5 minutes, at about 260° C. in 3–4 minutes, at about 270° C. in 2–3 minutes, and at about 280° C. in about 2 minutes, respectively to lose its adhesiveness. The urea supplied at a designed proportion to the recycling amount of the crude cyanuric acid in the reaction vessel under agitation becomes, after lapse of the abovedescribed solidifying time, freely flowable powdery and granular crude cyanuric acid having no adhesiveness. Further, when, at this time, the urea of the designed amount is supplied again, there is obtained after the abovementioned solidifying time the similar freely flowable crude cyanuric acid. Further, on repetition of the similar operation, similar results are obtained. Accordingly, it will be understood that, by charging the urea into the same reaction vessel divisionally at the designed interval, the combined amount of supply of the urea can be increased by more than ⅓ in ration by weight to the recycling amount of the crude cyanuric acid.

To set the distance of the urea supply port to a condition at which the residence time for the contents to exceed 20 minutes will not only lead to an excessive enlargement of the reaction vessel but also to an increased volatilization and dissipation of volatile matter to cause lowering of yield, which is undesirable.

The crude cyanuric acid to be produced according to the process of the present invention comprises cyanuric acid as its main component. But, as it contains a small amount of ammelide, ammeline, biuret and unreacted urea as impurities, it should be refined with an aqueous solution of mineral acid such as sulfuric acid, hydrochloric acid, etc. for use as a product.

In carrying out the present invention, crude cyanuric acid or purified crude cyanuric acid according to necessity is previously put into the aforementioned reaction vessel provided with agitator, either molten urea, granular urea (crystalline urea) or aqueous solution of urea is supplied from the respective urea supply port to have the urea decomposed under heat, then a part of the formed crude cyanuric acid is recycled into said reaction vessel. In so doing, there must be provided at each urea supply port a flow regulating valve to control the ratio of mixing of the crude cyanuric acid to the supplied urea so that it should remain within the designed range.

In case of using an aqueous solution of urea as a material, the water content should be retained within the range of 30%.

In the present invention process, in case of using a urea containing biuret, the speed of progress of reaction is accelerated, hence the amount of supply can be further increased.

In case of using a liquid state urea such as molten urea or an aqueous solution of urea for supply to the reaction vessel, it is suitable to use a reaction vessel as shown in the drawing.

Reaction vessel 1 is furnished with a jacket, through which a heating medium passes. To one end of the agitator shaft 2 a rotary joint 11 is connected. Rotary joint 11 is integrally connected with outlet **19*a* and inlet 20*a* for the heating medium led to agitator shaft 2 and agitator blades 3. Reaction vessel 1 is also provided with outlet 19*b* and inlet 20*b* for the heating medium. Agitator shaft 2 is driven by motor 14 mediated by chain drive 15. At both ends of the reaction vessel 1 stuffing boxes 12, 13 for sealing the agitator shaft 2 are provided. On the upper surface of the reaction vessel 1 there are provided recycled product inlet 8 disposed at the beginning position in the conveyance direction of the contents, exhaust duct 21, and ten material urea supply ports 22 disposed with designed intervals, respectively. To the terminal end position of the reaction vessel 1 a product discharge chute 18 is integrally provided. A part of the product discharged through the product chute 18 is recycled by the recycle screw 4 through the slide gate 9 to the reaction vessel 1 from the recycled product inlet 8, and other part of the above product is recovered through the rotary valve 10. The recycle screw 4 is driven by the motor 16 mediated by the chain drive 17. Each urea supply port 22 is connected with a supply pipe 23 furnished with liquid urea flow meter 6 and liquid urea flow control valve 7. All the supply pipes 23 are connected with the liquid urea supply pump 5, mediated by a supply pipe 25 furnished with a liquid urea flow meter 24. Liquid urea is continuously supplied by the liquid urea supply pump 5 through the respective urea supply ports 22 into the reaction vessel 1 and the supply volume of the urea is controlled by the liquid urea flow control valve 7. Temperature of the contents in the reaction vessel 1** is detected by the thermometers $T_1$–$T_{11}$.

In case of using crystalline urea in the abovementioned reaction vessel, operation can be made in the same procedures as in the case of using the liquid urea by using constant mass feeding devices such as a vibrating feeder or a screw feeder instead of supply pump, liquid urea flow meters and liquid urea flow control valves.

The process of the present invention will become more apparent from the following Example and Comparative Example.

EXAMPLE

The abovementioned reaction vessel having the heat transfer area of about 2 $m^2$ and the effective volume of about 65 liters was used. While leading a heating medium through the reaction vessel, agitator shaft was rotated at 40 r.p.m. (variable) to start agitation. Crude cyanuric acid (cyanuric acid 73.02%, ammelin and ammelide in total 26.48%, urea 0.46%, and biuret 0.04%) (30 kg) was charged to bring the temperature of the contents to about 260° C. Then, crude cyanuric acid was additionally charged at the rate of 18 kg/hour, and the crude cyanuric acid discharged from the product discharge chute was recycled into the reactor at the same rate. At that time, the temperature of the crude cyanuric acid was about 270° C. near the product discharge chute, and about 262° C. at the recycled product inlet.

Then, under the continuous maintenance of recycling of crude cyanuric acid, the molten urea heated for 1 hour at the temperature of 160° C. was continuously supplied at the rate of 6 kg/hour from each of the three material urea supply ports out of the 10 supply ports provided in series on the upper cover of the reactor.

In the above process, the intervals of the urea supply ports were so set that the position at which the recycled crude cyanuric acid is kept staying for about 2 minutes from its supply port was determined as the first urea supply port, the position at which the urea supplied to the first urea supply port stays for about 6 minutes was determined as the second urea supply port, the position at which the urea supplied to the second urea supply port stays for about 6 minutes was determined as the third urea supply port, and the residence time of the contents from the third urea supply port to the product discharge chute was set at about 75 minutes, and further, the residence time of the recycled crude cyanuric acid in the reaction vessel was set at about 90 minutes. With these time settings, heat decomposition of urea was conducted.

When the reaction was effected under the above condition, steady state was reached about 4 hours after the start of supply of the urea. The material urea was continuously supplied at the rate of 18 kg/hour from the three supply ports. On the other hand, crude cyanuric acid was continuously discharged from the product discharge chute at the rate of 29.2 kg/hour. Of the thus obtained crude cyanuric acid, the portion corresponding to 18 kg/hour was continuously recycled to the reactor, and the remaining crude cyanuric acid which was continuously discharged from the product discharge chute was recovered as product at the rate of 11.2 kg/hour.

The discharge temperature of the crude cyanuric acid under the steady state was 268° C.–270° C. The temperature of the contents immediately before the first urea supply port was 262° C.–264° C. The temperature of the contents immediately before the second urea supply port was 256° C.–258° C. The temperature of the contents immediately before the third urea supply port was 254° C.–256° C.

As a result of the 12 hours' continuous operation from the attainment of the steady state, against the urea of 227 kg supplied during the time, crude cyanuric acid of 134.4 kg was obtained as a product. The product had a mean particle diameter of about 580 microns in harmonic mean diameter. The particles having the diameter of more than 2 mm $\phi$ were no more than 2.5% by weight of the whole product obtained. Their average composition was cyanuric acid 72.82%, ammelin and ammelide in total 26.67%, urea 0.48%, and biuret 0.03%.

By boiling the resulting crude cyanuric acid (11.2 kg) in an aqueous solution of 10% sulfuric acid, crude cyanuric acid having more than 99.5% purity (11.1 kg) was obtained. Accordingly, the yield of the cyanuric acid to the urea supply amount corresponds to 81.9%. If the portion of urea which was volatilized to dissipate from the reactor was recovered, the yield of the cyanuric acid could be further increased.

According to the present Example, by supplying the urea at the rate of $\frac{1}{3}$ part by weight to 1 part by weight of crude cyanuric acid recycled into the reactor from each of the three urea supply ports, ultimately it was possible to supply the same amount of urea to 1 part by weight of the recycling amount of crude cyanuric acid to effect continuous heat treatment.

Comparative Example

In the same manner as in the foregoing Example, crude cyanuric acid was recycled into the reactor at the rate of 18 kg/hour and continuously supplied the molten urea heated for 1 hour at the temperature of 160° C., said supply being made at the rate of 9 kg/hour from one urea supply port. About 1 hour after the start of supply of the urea, adhesion of reaction product occurred in the vicinity or the urea supply port, making it unavoidable to stop operation. Thus, it was in fact impossible to carry on continuous operation.

According to the present invention process, in mixing the crude cyanuric acid with the urea and heating the mixture, the urea can be supplied in the same or more proportion in ratio by weight to the crude cyanuric acid to be recycled to effect continuous operation. This makes it possible to render the reaction vessel compact to reduce installation cost and further to minimize loss of energy and improve heat efficiency, thus providing the remarkable effect in practice.

What is claimed is:

1. A process for producing cyanuric acid from urea comprising the steps of:

providing an externally heated reaction vessel, said reaction vessel having agitating means for agitating the contents of said vessel and a plurality of urea supply ports for supplying urea into said vessel, the supply ports being spaced along said vessel at intervals such that the residence time of urea supplied through said ports in said vessel varies from 2–20 minutes;

charging said reactor with cyanuric acid, heating said vessel and bringing said cyanuric acid within the vessel to a constant temperature;

after reaching constant temperature, withdrawing an amount of cyanuric acid from said vessel and recycling it thereinto;

supplying urea into said vessel through said plurality of supply ports simultaneously with said recycling of cyanuric acid, the amount of urea supplied through each supply port being not greater than $\frac{1}{3}$ X, where X is the amount of cyanuric acid recycled into said vessel; and, withdrawing cyanuric acid product from said vessel following the introduction of said urea into said vessel.

2. A process as claimed in claim 1, wherein said reactor vessel is heated to a temperature of 230–320? C.

3. A process as claimed in claim 1, wherein said cyanuric acid charged into said reactor is crude cyanuric acid.

4. A method as claimed in claim 1, wherein cyanuric acid initially charged into said reactor is purified cyanuric acid.

5. A process as claimed in claim 1, wherein said urea supplied into said vessel through said urea supply ports is molten urea.

6. A process as claimed in claim 1, wherein said urea supplied into said vessel through said supply ports is granular urea.

7. A process as claimed in claim 1, wherein said urea supplied into said vessel through said supply ports is an aqueous solution of urea having not greater than 30% water content.

8. A process as claimed in claim 1, wherein said urea supplied into said vessel through said supply ports contains buiret.

9. A process as claimed in claim 1, further providing a regulating means at each urea supply port for controlling the amount of urea supplied to said vessel through each supply port.

10. A process as claimed in claim 1, wherein said reactor vessel has heat transfer areas along the inner wall and agitator means thereof.

* * * * *